(12) United States Patent
Gibson

(10) Patent No.: US 8,692,073 B2
(45) Date of Patent: Apr. 8, 2014

(54) CRISPERS LETTUCE VARIETY

(75) Inventor: G. Darryn Gibson, Prunedale, CA (US)

(73) Assignee: Progeny Advanced Genetics, Salinas, CA (US)

( * ) Notice: Subject to any disclaimer, the term of this patent is extended or adjusted under 35 U.S.C. 154(b) by 376 days.

(21) Appl. No.: 13/117,620

(22) Filed: May 27, 2011

(65) Prior Publication Data

US 2011/0296559 A1    Dec. 1, 2011

Related U.S. Application Data

(60) Provisional application No. 61/396,537, filed on May 28, 2010.

(51) Int. Cl.
*A01H 1/00* (2006.01)
*A01H 4/00* (2006.01)
*A01H 5/00* (2006.01)
*A01H 5/10* (2006.01)
*C12N 15/82* (2006.01)

(52) U.S. Cl.
USPC ........... 800/305; 800/260; 800/278; 800/298; 435/410; 435/419; 435/430

(58) Field of Classification Search
None
See application file for complete search history.

(56) References Cited

U.S. PATENT DOCUMENTS

2012/0011612 A1 *  1/2012  Skrsyniarz ................... 800/265

* cited by examiner

*Primary Examiner* — Eileen B O Hara
(74) *Attorney, Agent, or Firm* — Morrison & Foerster LLP

(57) ABSTRACT

A new and distinct lettuce variety designated 'Crispers', characterized by having a distinct thick leaf texture, symmetrical and compact leaf, lack of an obvious mid-rib, a short open growth habit, and undulating leaf margins shape, and improved shelf life in a non-heading variety.

Figure 1:

11 Claims, 2 Drawing Sheets
(2 of 2 Drawing Sheet(s) Filed in Color)

CRISPERS LETTUCE VARIETY

CROSS REFERENCE TO RELATED APPLICATIONS

This application claims the benefit under 35 USC 119(e) of prior copending U.S. Provisional Patent Application No. 61/396,537, filed May 28, 2010, the disclosure of which is hereby incorporated by reference in its entirety

FIELD

This invention relates to the field of plant breeding. In particular, this invention relates to a new lettuce, *Lactuca sativa* variety designated 'Crispers'.

BACKGROUND

Lettuce is an increasingly popular crop. Worldwide lettuce consumption continues to increase. As a result of this demand, there is a continued need for new lettuce varieties. Presently, there are over a thousand known lettuce varieties which can be sub-divided into two different groups depending on heading characteristic: tight heading vs. non-heading. The drawback with most presently available lettuce varieties is the tight heading characteristic which prevents the removal of individual leaves, making these varieties unsuitable for the emerging whole leaf lettuce market. Further, the whole leaf lettuce market has been limited to the use of loose leaf and romaine lettuce types, and is not economically feasible for iceberg or other heading lettuces, as the tight heading characteristics of these lettuce types prevent the removal of individual leaves. Among the basic traits a lettuce variety needs to possess to be considered in the whole leaf lettuce market are a non-heading characteristic and an open growth habit, so that the leaves can be easily removed from the core or stem. The variety also must have a durable thick leaf texture and reduced or absent mid-rib, as the leaves must undergo one of many mechanical processes of being removed, washed, and dried without cracking or breaking. Typically, decay of the lettuce product starts on the thin areas of the leaf margins and in the mid-rib. In particular, there is a need for improved green leaf lettuce varieties with a longer shelf life by eliminating the mid-rib and by producing a thicker leaf structure.

SUMMARY

In order to meet these needs, the present invention is directed to an improved green leaf lettuce variety as a result of a cross between a romaine lettuce variety and a green leaf lettuce variety, with a distinct compact and open phenotype, comprised of thick leaf texture. The variety does not form a heart of a cup. The variety also lacks an obvious mid-rib. Additionally, the variety has a short open growth habit, and undulating leaf margins. Advantageously, the improved green leaf lettuce variety is suitable for the whole leaf lettuce market. In particular, the present invention is directed to lettuce, *Lactuca sativa*, seed designated 'Crispers' having ATCC Accession Number PTA-12098. The present invention is further directed to lettuce, *Lactuca sativa* plants and the lettuce heads produced therefrom produced by growing 'Crispers' lettuce seed.

The present invention is further directed to a *Lactuca sativa* plant and the lettuce head produced therefrom having all the physiological and morphological characteristics of a *Lactuca sativa* plant produced by growing 'Crispers' lettuce seed having ATCC Accession Number PTA-12098 [[X]]. The present invention is further directed to an $F_1$ hybrid lettuce, *Lactuca sativa* seed, plants grown from the seed and a head produced therefrom having 'Crispers' as a parent wherein 'Crispers' is grown from 'Crispers' lettuce seed having ATCC Accession Number PTA-12098.

The present invention is further directed to pollen and ovules produced by 'Crispers' lettuce plants. The present invention is further directed to tissue culture of 'Crispers' lettuce plants.

The present invention is further directed to a method of selecting lettuce plants including: a) growing 'Crispers' lettuce plants wherein the 'Crispers' plants are grown from lettuce seed having ATCC Accession Number PTA-12098, and b) selecting a plant from step a). The present invention is further directed to lettuce plants and seeds produced by the selected lettuce plants.

The present invention is further directed to a method of breeding lettuce plants including crossing a lettuce plant with a plant grown from 'Crispers' lettuce seed having ATCC Accession Number PTA-12098. The present invention is further directed to lettuce plants, heads from the lettuce plants and seeds produced therefrom where the lettuce plant is produced by the breeding method of the invention.

BRIEF DESCRIPTION OF THE PHOTOGRAPHS

The patent or application file contains at least one photograph executed in color. Copies of this patent or patent application publication with color drawings will be provided by the Office upon request and payment of the necessary fees.

FIG. 1. The first photograph shows a close-up top view perspective of a whole 'PX 254' plant lettuce variety grown in the field.

Figure 2:

FIG. 2. The second photograph shows a close-up view of the typical leaves of a 'PX 254' plant lettuce variety.

BRIEF DESCRIPTION OF THE TABLES

Table 1 shows plant measurement data from a field trial of 'Crispers' conducted in Salinas Valley Calif. in the summer of year 10.

Table 2 shows leaf measurement data from a field trial of 'Crispers' conducted in Salinas Valley Calif. in the summer of year 10.

Table 3 shows plant measurement data from a second field trial of 'Crispers' conducted in Salinas Valley Calif. in the summer of year 10.

Table 4 shows leaf measurement data from a second field trial of 'Crispers' conducted in Salinas Valley Calif. in the summer of year 10.

Table 5 shows plant measurement data from a field trial of 'Crispers' conducted in Yuma Ariz. in the fall of year 10.

Table 6 shows leaf measurement data from a field trial of 'Crispers' conducted in Yuma Ariz. in the fall of year 10.

Table 7 shows plant measurement data from a second field trial of 'Crispers' conducted in Yuma Ariz. in the fall of year 10.

Table 8 shows leaf measurement data from a second field trial of 'Crispers' conducted in Yuma Ariz. in the fall of year 10.

DETAILED DESCRIPTION

The present invention is directed to seeds of the lettuce variety 'Crispers', plants produced by growing 'Crispers' lettuce seeds, head isolated or harvested from the plants, one or more plants selected from a collection of 'Crispers' plants and seeds derived or produced therefrom; plants produced by crossing a lettuce plant with a 'Crispers' lettuce plant and seeds derived or produced therefrom.

Origin and Breeding History of the Variety 'Crispers'

'Crispers' is a green leaf lettuce variety developed from a hand pollinated cross of the romaine variety 'PRO 1377' available from Progeny Advanced Genetics, Inc., and the green leaf variety 'PRO 1202', a Progeny Advanced Genetics Inc. breeding line. The two parental varieties were selected for their slow growth, heavy leaf texture, tip burn resistance and bolting resistance. 'PRO 1377', a Florida type romaine variety, was selected for its improved leaf texture, tip burn resistance and bolting resistance. 'PRO 1202', a green leaf lettuce variety, was selected for its open growth habit, slow growth rate, tip burn and bolting resistance. The single seed descent and pedigree selection breeding methods were used after the cross was made to develop a unique green leaf variety with compact, thick textured and symmetrical leafs to be used as a whole leaf lettuce.

The utilized single seed descent method is a well known method of plant breeding. See, for example, *Heredity* (1975) 35, 211-219.

In year 1, a cross was made of the romaine variety 'PRO 1377', designated PSJV01E667, and the green leaf variety 'PRO 1202', in a summer research seed production field in San Joaquin Valley, Calif., designated research line number PSJV01E679. The $F_1$ seed was harvested in the fall of year 1 and designated as PSJV01E667 X PSJV01E679.

In late October of year 1, 40 $F_1$ seeds of PSJV01E667 X PSJV01E679 were planted in a green house facility in San Juan Bautista, Calif. At market stage all apparent self pollinated plants were removed and the remaining $F_1$ plants were allowed to self-pollinate. The resulting $F_2$ seed, indicated by research line number PSMG01P37, was harvested in bulk in late April of year 2. The seed was immediately cleaned, processed and prepared for planting.

A total of 200 random $F_2$ seeds of line number PSMG01P37 were planted in a summer research seed production field and redesignated as PSJV021233-1248. Segregation amongst the $F_2$ population was noted and all plants were allowed to self pollinate and produce seed. The $F_3$ seed from each plant was harvested and packaged individually in the fall of year 2. One seed from each package (individual plant) was removed and placed in one envelope, designated as PAUS021435-2, and planted in a research production field in the southern hemisphere. Segregation for phenotype and maturity was again evident and noted, and all plants were allowed to self-pollinate and produce seed. $F_4$ seed from 12 individual plants was harvested, cleaned and packaged individually.

The 12 $F_4$ lines, all from nonselected single $F_3$ plants of the pedigree 'PRO 1377' X 'PRO 1202' were received and processed in May of year 3. A trial was prepared (trial number 42-03) containing each of the 12 $F_4$ individual lines, as well as other new $F_4$ green leaf lines and the parent and industry standard varieties as checks. Research trial number 42-03 was planted in the Salinas Valley of California in the summer of year 3 and evaluated in the early fall. The $F_4$ lines were evaluated based on unique and distinct phenotypes, in addition to improved tolerances to tip burn and bolting when compared to the parent check varieties. Due to the heterozygosity of the parent lines, the $F_4$ lines were not uniform and segregated for phenotype, tip burn and bolting resistance. Multiple individual plant selections were made from the trial, and plants of unique phenotype, and improved tip burn and bolting resistance were selected, removed from the trial and allowed to seed in a green house facility. The $F_5$ seed from these individual plant selections was harvested in late year 3.

A sample of the remnant $F_5$ seed from each of the selected plants was then planted in a research seed production field in the spring of year 5. Each of the individual lines was rogued for phenotype and maturity, at various stages of growth, and all offtypes and variants were removed. The remaining plants in each of the individual blocks were allowed to self pollinate, and the $F_6$ seed from each block was harvested in mass.

After processing, the new F6 green leaf lines were trialed together along with their parent varieties and industry standards throughout the summer and fall of year 6 and year 7 in the production regions of California and Ariz. The $F_6$ lines were evaluated in multiple trials and rated based on unique phenotype, genetic uniformity, incidence and severity of tip burn, and field holding ability as compared to each other and their parent varieties. After the completion of multiple trial evaluations the line designated PSJV 05 4134 stood out as possessing a unique and distinct phenotype, having a compact and open growth habit, heavy textured symmetrical leafs, and improved resistance to tip burn and bolting.

Based on the year 6 and year 7 trialing results, the variety was designated as 'PX 254' in year 7.

$F_7$ seed of 'PX 254' was produced in a research and development seed production field in the summer of year 8 and a commercial increase, producing $F_8$ seed, was carried out in year 9.

'PX 254' being a unique and distinct type of green leaf lettuce was trialed and shown to multiple lettuce shippers that specialize in the whole leaf lettuce market. After multiple field and processing tests the variety proved to be suited to the whole leaf market based on its improved leaf texture, its symmetrical leaf shape, and its improved shelf life.

Based on the continued performance of the variety, 'PX 254' was designated 'Crispers' in the summer of year 10.

As evaluated in multiple seed production fields and large trials, the $F_7$ and $F_8$ generations of seed from the variety 'Crispers' have been uniform and stable.

The 'Crispers' green leaf lettuce variety has novel characteristics that distinguish it from all other lettuce varieties. Romaine lettuce varieties most closely resemble the 'Crispers' green leaf lettuce variety. However, 'Crispers' is still quite different from the romaine lettuce varieties. As compared to the romaine lettuce varieties, 'Crispers' is shorter, does not form a heart or cup, and lacks a prominent mid rib. Additionally, 'Crispers' is suitable for the whole leaf lettuce market.

The selected 'Crispers' green leaf lettuce variety seed produces a lettuce plant comprising a thick leaf texture, lack of an obvious mid-rib, short open growth habit, and undulating leaf margins. In one embodiment, the leaf size of more than 12 leafs per plant is about 5 inches in length and about 4 inches in width, when the head weighs between 5 and 7 ounces.

Breeding and Selection

The present invention is further directed to the use of 'Crispers' lettuce in breeding and selection of new varieties.

A. Breeding

In lettuce breeding, lines are selected for certain desired appropriate characteristics.

To optimize crossing, it is important to note that lettuce is an obligate self-pollinating species. This means that the pollen is shed before stigma emergence, assuring 100% self-fertilization. Since each lettuce flower is an aggregate of about 10-20 individual florets (typical of the Compositae family), manual removal of the anther tubes containing the pollen is performed by procedures well known in the art of lettuce breeding.

The manual removal of anther tubes, though an effective means to ensure the removal of all self-pollinating possibilities, is very tedious and time consuming when a large number of crosses are to be made. The breeders have therefore adapted a well documented and modified method of making crosses more efficiently using these methods. This particular cross was made by first misting the designated male flowers to wash the pollen off prior to fertilization. This process of misting is a proven and effective means of pollen removal that assures crossing or hybridization. About 60-90 minutes past sunrise, flowers to be used for crossings are selected. The basis for selection are open flowers, with the stigma emerged and the pollen visibly attached to the single stigma (about 10-20 stigma). Using 3-4 pumps of water from a regular spray bottle, the pollen is washed off with enough pressure to dislodge the pollen grains, but not enough to damage the style. Excess water is dried off with clean paper towels. About 30 minutes later, the styles should spring back up and the two lobes of the stigma are visibly open in a "V" shape. Pollen from another variety or donor parent is then introduced by gently rubbing the stigma and style of the donor parent to the maternal parent. Tags with the pertinent information on date and pedigree are then secured to the flowers in order to keep track.

About 3 weeks after pollination, seeds are harvested when the involucre have matured. The seeds are eventually sown and in the presence of markers such as leaf color or leaf margins, the selfed or maternal seedlings or plants are identified. Generally, there are no visible markers and breeders must wait until the $F_2$ generations when expected segregation patterns for the genetic character of interest can be followed. This latter situation mandates a lengthy wait to determine if hybrids are produced. Two relevant references teaching methods for out crossing lettuce are: (1) Ryder, E. J. and A. S. Johnson. 1974. Mist depollination of lettuce flowers. Hortscience 9:584; and (2) Nagata, R. T. 1992. Clip and Wash Method of Emasculation for Lettuce. Hortscience 27(8):907-908 both of which are hereby incorporated by reference in their entirety for the purpose of providing details on the techniques well known in the art. In the present invention, Para Cos and Frontier Cos were crossed.

B. Selection

In addition to crossing, selection may be used to identify and isolate new lettuce lines. In lettuce selection, lettuce seeds are planted, the plants are grown and single plant selections are made of plants with desired characteristics. Such characteristics may include improved head and frame size, deeper or darker green leaf color, etc. Seed from the single plant selections are harvested, separated from seeds of the other plants in the field and re-planted. The plants from the selected seed are monitored to determine if they exhibit the desired characteristics of the originally selected line. Selection work is continued over multiple generations to increase the uniformity of the new line.

DEPOSIT INFORMATION

Applicants have made available to the public without restriction a deposit of at least 2500 seeds of lettuce variety 'Crispers' with the American Type Culture Collection (ATCC), P.O. Box 1549, MANASSAS, VA 20108 USA, with a deposit on Sep. 19, 2011 which has been assigned ATCC number PTA-12098. This deposit of the lettuce variety 'Crispers' will be maintained in the ATCC depository, which is a public depository, for a period of 30 years, or 5 years after the most recent request, or for the effective life of the patent, whichever is longer, and will be replaced if it becomes nonviable during that period. Additionally, Applicants have satisfied all the requirements of 37 C.F.R. §§1.801-1.809, including providing an indication of the viability of the sample. Applicants impose no restrictions on the availability of the deposited material from the ATCC; however, Applicants have no authority to waive any restrictions imposed by law on the transfer of biological material or its transportation in commerce. Applicants do not waive any infringement of its rights granted under this patent or under the Plant Cultivar Protection Act (7 USC 2321 et seq.).

The deposit will be maintained in the ATCC depository, which is a public depository, for a period of 30 years, or 5 years after the most recent request, or for the effective life of the patent, whichever is longer, and will be replaced if a deposit becomes nonviable during that period.

EXAMPLE

The following non-limiting Example is provided to demonstrate and illustrate certain preferred embodiments and aspects of the present disclosure and should not be construed as limiting.

Plant and leaf physical characteristics of the 'Crispers' green leaf lettuce variety were measured from field trials conducted in the summer of year 10 in Salinas Valley Calif. (Tables 1-4), and in the fall of year 10 in Yuma, Ariz. (Tables 5-8). Plant characteristics that were measured include core diameter and length, plant height and weight, frame diameter, and leaf counts per plant. Leaf characteristics that were measured include length, width, thickness, and weight.

TABLE 1

| Plant Sample No. | Core Diameter (mm) | Core Length (mm) | Plant Height (mm) | Frame Diameter (cm) | Plant Weight (g) | Leaf Count/Plant |
|---|---|---|---|---|---|---|
| 1 | 19 | 20 | 152 | 20 | 322 | 22 |
| 2 | 22 | 20 | 156 | 20 | 318 | 22 |
| 3 | 20 | 25 | 150 | 25 | 315 | 22 |
| 4 | 25 | 25 | 150 | 25 | 389 | 21 |
| 5 | 19 | 25 | 150 | 18 | 325 | 25 |
| 6 | 19 | 20 | 148 | 19 | 268 | 24 |
| 7 | 20 | 22 | 146 | 15 | 325 | 25 |
| 8 | 20 | 22 | 145 | 18 | 336 | 24 |
| 9 | 20 | 21 | 139 | 19 | 325 | 23 |
| 10 | 20 | 21 | 150 | 19 | 321 | 23 |
| 11 | 20 | 20 | 150 | 19 | 318 | 23 |
| 12 | 25 | 20 | 156 | 22 | 323 | 21 |

TABLE 1-continued

| Plant Sample No. | Core Diameter (mm) | Core Length (mm) | Plant Height (mm) | Frame Diameter (cm) | Plant Weight (g) | Leaf Count/ Plant |
|---|---|---|---|---|---|---|
| 13 | 25 | 25 | 150 | 21 | 387 | 22 |
| 14 | 25 | 25 | 150 | 23 | 380 | 22 |
| 15 | 20 | 20 | 156 | 25 | 302 | 24 |
| 16 | 20 | 20 | 156 | 25 | 365 | 24 |
| 17 | 20 | 20 | 154 | 25 | 385 | 23 |
| 18 | 25 | 23 | 150 | 23 | 365 | 24 |
| 19 | 22 | 22 | 152 | 20 | 326 | 23 |
| 20 | 22 | 22 | 152 | 21 | 354 | 21 |
| 21 | 22 | 19 | 152 | 22 | 318 | 21 |
| 22 | 25 | 21 | 156 | 22 | 333 | 22 |
| 23 | 25 | 22 | 149 | 18 | 341 | 22 |
| 24 | 25 | 22 | 142 | 16 | 385 | 22 |
| Average | 20.8 | 21.8 | 149.3 | 19.9 | 323.8 | 23 |
| Standard Dev | 2.14E+00 | 2.09E+00 | 4.64E+00 | 2.87E+00 | 2.64E+01 | 1.38E+00 |

TABLE 2

| Leaf Sample No. | Leaf Length (mm) | Leaf Width (mm) | Leaf Thickness (mm) | Leaf Weight (g) |
|---|---|---|---|---|
| 1 | 145 | 190 | 0.83 | 18.00 |
| 2 | 155 | 210 | 0.85 | 16.00 |
| 3 | 145 | 180 | 0.91 | 14.00 |
| 4 | 144 | 160 | 0.86 | 14.00 |
| 5 | 144 | 190 | 0.95 | 15.00 |
| 6 | 145 | 150 | 0.90 | 16.00 |
| 7 | 140 | 180 | 0.78 | 16.00 |
| 8 | 140 | 190 | 0.75 | 16.00 |
| 9 | 139 | 165 | 0.78 | 18.00 |
| 10 | 149 | 185 | 0.76 | 18.00 |
| 11 | 148 | 160 | 0.74 | 18.00 |
| 12 | 148 | 180 | 0.75 | 15.00 |
| 13 | 156 | 190 | 0.75 | 16.00 |
| 14 | 152 | 210 | 0.74 | 13.00 |
| 15 | 156 | 180 | 0.85 | 12.00 |
| 16 | 157 | 160 | 0.62 | 18.00 |
| 17 | 140 | 190 | 0.75 | 18.00 |
| 18 | 155 | 150 | 0.85 | 12.00 |
| 19 | 155 | 180 | 0.75 | 12.00 |
| 20 | 124 | 190 | 0.76 | 8.00 |
| 21 | 118 | 165 | 0.74 | 9.00 |
| 22 | 154 | 185 | 0.79 | 10.00 |
| 23 | 136 | 160 | 0.80 | 12.00 |
| 24 | 158 | 180 | 0.85 | 18.00 |
| Average | 145 | 178 | 0.82 | 16.17 |
| Standard Dev | 4.49E+00 | 1.68E+01 | 7.20E−02 | 1.53E+00 |

TABLE 3

| Plant Sample No. | Core Diameter (mm) | Core Length (mm) | Plant Height (mm) | Frame Diameter (cm) | Plant Weight (g) | Leaf Count/ Plant |
|---|---|---|---|---|---|---|
| 1 | 22 | 21 | 148 | 21 | 325 | 20 |
| 2 | 22 | 22 | 146 | 20 | 318 | 20 |
| 3 | 25 | 22 | 145 | 20 | 365 | 20 |
| 4 | 25 | 25 | 145 | 21 | 325 | 22 |
| 5 | 24 | 25 | 145 | 19 | 325 | 22 |
| 6 | 24 | 25 | 147 | 18 | 367 | 21 |
| 7 | 23 | 21 | 145 | 18 | 289 | 21 |
| 8 | 22 | 21 | 145 | 19 | 245 | 22 |
| 9 | 22 | 21 | 148 | 20 | 215 | 22 |
| 10 | 22 | 21 | 150 | 20 | 321 | 22 |
| 11 | 25 | 20 | 145 | 21 | 365 | 22 |
| 12 | 24 | 19 | 152 | 21 | 324 | 20 |
| 13 | 22 | 19 | 152 | 20 | 289 | 22 |
| 14 | 22 | 21 | 153 | 24 | 214 | 22 |
| 15 | 22 | 18 | 145 | 21 | 256 | 20 |
| 16 | 22 | 19 | 149 | 21 | 287 | 20 |
| 17 | 22 | 21 | 153 | 20 | 269 | 20 |
| 18 | 26 | 19 | 157 | 20 | 386 | 21 |
| 19 | 25 | 20 | 148 | 19 | 325 | 20 |
| 20 | 25 | 21 | 152 | 18 | 268 | 22 |
| 21 | 24 | 21 | 150 | 19 | 295 | 22 |
| 22 | 24 | 19 | 148 | 19 | 335 | 22 |
| 23 | 25 | 19 | 152 | 20 | 333 | 21 |
| 24 | 25 | 21 | 149 | 22 | 234 | 20 |

TABLE 3-continued

| Plant Sample No. | Core Diameter (mm) | Core Length (mm) | Plant Height (mm) | Frame Diameter (cm) | Plant Weight (g) | Leaf Count/Plant |
| --- | --- | --- | --- | --- | --- | --- |
| Average | 23.3 | 21.9 | 146.8 | 19.8 | 315.3 | 21 |
| Standard Dev | 1.30E+00 | 2.02E+00 | 2.34E+00 | 1.11E+00 | 4.64E+01 | 9.37E−01 |

TABLE 4

| Leaf Sample No. | Leaf Length (mm) | Leaf Width (mm) | Leaf Thickness (mm) | Leaf Weight (g) |
| --- | --- | --- | --- | --- |
| 1 | 145 | 176 | 0.86 | 16.00 |
| 2 | 138 | 185 | 0.84 | 14.00 |
| 3 | 136 | 165 | 0.85 | 14.00 |
| 4 | 145 | 165 | 0.85 | 18.00 |
| 5 | 145 | 164 | 0.75 | 14.00 |
| 6 | 142 | 165 | 0.76 | 13.00 |
| 7 | 143 | 172 | 0.85 | 13.00 |
| 8 | 142 | 165 | 0.85 | 13.00 |
| 9 | 140 | 156 | 0.85 | 14.00 |
| 10 | 139 | 168 | 0.86 | 13.00 |
| 11 | 136 | 149 | 0.83 | 14.00 |
| 12 | 138 | 167 | 0.75 | 13.00 |
| 13 | 136 | 168 | 0.72 | 13.00 |
| 14 | 135 | 166 | 0.78 | 15.00 |
| 15 | 136 | 166 | 0.75 | 18.00 |
| 16 | 132 | 165 | 0.82 | 18.00 |
| 17 | 13 | 145 | 0.84 | 13.00 |
| 18 | 132 | 170 | 0.82 | 15.00 |
| 19 | 140 | 170 | 0.85 | 18.00 |
| 20 | 140 | 171 | 0.85 | 16.00 |
| 21 | 136 | 168 | 0.89 | 16.00 |
| 22 | 135 | 168 | 0.92 | 14.00 |
| 23 | 135 | 166 | 0.92 | 15.00 |
| 24 | 132 | 165 | 0.96 | 16.00 |
| Average | 141 | 166 | 0.83 | 14.83 |
| Standard Dev | 3.39E+00 | 9.03E+00 | 4.40E−02 | 1.51E+00 |

TABLE 5

| Plant Sample No. | Core Diameter (mm) | Core Length (mm) | Plant Height (mm) | Frame Diameter (cm) | Plant Weight (g) | Leaf Count/Plant |
| --- | --- | --- | --- | --- | --- | --- |
| 1 | 22 | 19 | 149 | 19 | 400 | 21 |
| 2 | 22 | 19 | 149 | 19 | 400 | 22 |
| 3 | 21 | 21 | 152 | 18 | 325 | 22 |
| 4 | 21 | 21 | 151 | 18 | 365 | 22 |
| 5 | 20 | 29 | 151 | 18 | 387 | 21 |
| 6 | 25 | 25 | 152 | 19 | 365 | 21 |
| 7 | 24 | 15 | 149 | 22 | 324 | 23 |
| 8 | 24 | 15 | 149 | 22 | 410 | 23 |
| 9 | 23 | 18 | 148 | 25 | 326 | 22 |
| 10 | 23 | 18 | 147 | 19 | 357 | 22 |
| 11 | 22 | 20 | 150 | 21 | 368 | 23 |
| 12 | 22 | 22 | 150 | 20 | 298 | 23 |
| 13 | 21 | 22 | 152 | 23 | 325 | 22 |
| 14 | 21 | 22 | 152 | 23 | 302 | 22 |
| 15 | 20 | 20 | 149 | 24 | 364 | 21 |
| 16 | 20 | 21 | 148 | 19 | 319 | 23 |
| 17 | 20 | 25 | 147 | 21 | 384 | 23 |
| 18 | 20 | 22 | 147 | 25 | 298 | 23 |
| 19 | 21 | 22 | 145 | 24 | 285 | 22 |
| 20 | 20 | 21 | 146 | 23 | 410 | 21 |
| 21 | 20 | 24 | 148 | 23 | 394 | 20 |
| 22 | 23 | 22 | 149 | 24 | 348 | 20 |
| 23 | 23 | 22 | 150 | 25 | 326 | 21 |
| 24 | 22 | 24 | 146 | 25 | 309 | 22 |
| Average | 22.4 | 20.2 | 149.8 | 20.0 | 360.4 | 22 |
| Standard Dev | 1.44E+00 | 3.95E+00 | 1.54E+00 | 2.13E+00 | 3.58E+01 | 7.93E−01 |

TABLE 6

| Leaf Sample No. | Leaf Length (mm) | Leaf Width (mm) | Leaf Thickness (mm) | Leaf Weight (g) |
| --- | --- | --- | --- | --- |
| 1 | 144 | 150 | 0.85 | 14.00 |
| 2 | 143 | 150 | 0.86 | 14.00 |
| 3 | 145 | 150 | 0.85 | 14.00 |
| 4 | 145 | 148 | 0.85 | 14.00 |
| 5 | 139 | 149 | 0.84 | 13.00 |

TABLE 6-continued

| Leaf Sample No. | Leaf Length (mm) | Leaf Width (mm) | Leaf Thickness (mm) | Leaf Weight (g) |
| --- | --- | --- | --- | --- |
| 6 | 145 | 146 | 0.87 | 13.00 |
| 7 | 140 | 145 | 0.85 | 14.00 |
| 8 | 142 | 149 | 0.85 | 15.00 |
| 9 | 142 | 149 | 0.85 | 16.00 |
| 10 | 141 | 150 | 0.89 | 14.00 |
| 11 | 141 | 147 | 0.75 | 13.00 |
| 12 | 140 | 150 | 0.78 | 12.00 |
| 13 | 145 | 151 | 0.86 | 12.00 |
| 14 | 146 | 143 | 0.84 | 12.00 |
| 15 | 146 | 147 | 0.82 | 11.00 |
| 16 | 145 | 159 | 0.80 | 10.00 |
| 17 | 142 | 154 | 0.80 | 11.00 |
| 18 | 139 | 149 | 0.85 | 11.00 |
| 19 | 145 | 152 | 0.89 | 12.00 |
| 20 | 136 | 158 | 0.75 | 14.00 |
| 21 | 138 | 156 | 0.78 | 15.00 |
| 22 | 145 | 159 | 0.85 | 12.00 |
| 23 | 135 | 157 | 0.80 | 15.00 |
| 24 | 140 | 141 | 0.82 | 15.00 |
| Average | 142 | 149 | 0.83 | 13.83 |
| Standard Dev | 2.14E+00 | 1.73E+00 | 3.82E−02 | 1.03E+00 |

TABLE 7

| Plant Sample No. | Core Diameter (mm) | Core Length (mm) | Plant Height (mm) | Frame Diameter (cm) | Plant Weight (g) | Leaf Count/ Plant |
| --- | --- | --- | --- | --- | --- | --- |
| 1 | 20 | 20 | 146 | 21 | 325 | 22 |
| 2 | 24 | 21 | 146 | 21 | 362 | 22 |
| 3 | 24 | 24 | 148 | 21 | 354 | 22 |
| 4 | 24 | 24 | 140 | 22 | 378 | 21 |
| 5 | 23 | 25 | 141 | 21 | 301 | 23 |
| 6 | 24 | 25 | 147 | 21 | 368 | 23 |
| 7 | 21 | 25 | 142 | 20 | 325 | 21 |
| 8 | 24 | 25 | 139 | 20 | 306 | 23 |
| 9 | 24 | 20 | 134 | 20 | 398 | 23 |
| 10 | 21 | 23 | 141 | 20 | 410 | 21 |
| 11 | 20 | 26 | 148 | 24 | 401 | 21 |
| 12 | 23 | 24 | 135 | 23 | 368 | 21 |
| 13 | 20 | 23 | 145 | 20 | 365 | 22 |
| 14 | 20 | 20 | 132 | 21 | 398 | 22 |
| 15 | 20 | 20 | 139 | 21 | 302 | 21 |
| 16 | 20 | 25 | 145 | 22 | 318 | 23 |
| 17 | 23 | 24 | 140 | 22 | 296 | 23 |
| 18 | 21 | 24 | 142 | 24 | 354 | 23 |
| 19 | 21 | 25 | 143 | 20 | 368 | 23 |
| 20 | 20 | 23 | 135 | 25 | 316 | 21 |
| 21 | 20 | 23 | 138 | 21 | 385 | 22 |
| 22 | 21 | 22 | 140 | 23 | 320 | 21 |
| 23 | 21 | 25 | 141 | 20 | 333 | 23 |
| 24 | 22 | 24 | 134 | 20 | 387 | 21 |
| Average | 22.7 | 23.5 | 142.3 | 21.2 | 358.0 | 22 |
| Standard Dev | 1.67E+00 | 2.07E+00 | 4.83E+00 | 1.27E+00 | 3.68E+01 | 9.00E−01 |

TABLE 8

| Leaf Sample No. | Leaf Length (mm) | Leaf Width (mm) | Leaf Thickness (mm) | Leaf Weight (g) |
| --- | --- | --- | --- | --- |
| 1 | 141 | 136 | 0.95 | 12.00 |
| 2 | 142 | 134 | 0.95 | 15.00 |
| 3 | 135 | 132 | 0.91 | 15.00 |
| 4 | 124 | 109 | 0.90 | 15.00 |
| 5 | 121 | 136 | 0.95 | 14.00 |
| 6 | 138 | 145 | 0.95 | 12.00 |
| 7 | 125 | 148 | 0.89 | 16.00 |
| 8 | 109 | 150 | 0.95 | 19.00 |
| 9 | 136 | 138 | 0.82 | 15.00 |

TABLE 8-continued

| Leaf Sample No. | Leaf Length (mm) | Leaf Width (mm) | Leaf Thickness (mm) | Leaf Weight (g) |
| --- | --- | --- | --- | --- |
| 10 | 108 | 126 | 0.86 | 16.00 |
| 11 | 124 | 134 | 0.87 | 15.00 |
| 12 | 103 | 136 | 0.86 | 14.00 |
| 13 | 125 | 134 | 0.85 | 14.00 |
| 14 | 135 | 150 | 0.85 | 13.00 |
| 15 | 135 | 123 | 0.85 | 12.00 |
| 16 | 136 | 134 | 0.92 | 11.00 |
| 17 | 118 | 101 | 0.95 | 14.00 |
| 18 | 120 | 134 | 0.95 | 14.00 |
| 19 | 121 | 127 | 0.90 | 15.00 |
| 20 | 112 | 150 | 0.90 | 15.00 |
| 21 | 108 | 139 | 0.90 | 13.00 |
| 22 | 138 | 159 | 0.89 | 13.00 |
| 23 | 136 | 148 | 0.89 | 18.00 |
| 24 | 120 | 146 | 0.87 | 15.00 |
| Average | 126 | 135 | 0.90 | 14.83 |
| Standard Dev | 1.34E+01 | 1.08E+01 | 4.56E−02 | 1.85E+00 |

Tables 1, 3, 5, and 7 show the results of the plant measurements of 'Crispers'. The samples had an average core diameter ranging from 20.8 mm to 23.3 mm, an average core length ranging from 20.2 mm to 23.5 mm, an average plant height ranging from 142.3 mm to 149.8 mm, an average frame diameter ranging from 19.8 mm to 21.2 mm, an average plant weight ranging from 315.3 g to 360.4 g, and an average leaf counts per plant that ranged from 21 to 23.

Tables 2, 4, 6, and 8 show the results of the leaf measurements of 'Crispers'. The samples had an average leaf length ranging from 126 mm to 145 mm, an average leaf width ranging from 135 mm to 178 mm, an average leaf thickness ranging from 0.82 mm to 0.90 mm, and an average leaf weight ranging from 13.83 g to 16.17 g.

Although the foregoing invention has been described in some detail by way of illustration and examples for purposes of clarity and understanding, it will be obvious that certain modifications and alternative embodiments of the invention are contemplated which do not depart from the spirit and scope of the invention as defined by the foregoing teachings and appended claims.

What is claimed:

1. Lettuce seed designated as 'Crispers' having ATCC Accession Number PTA-12098.
2. A lettuce plant produced by growing the seed of claim 1.
3. A lettuce head isolated from the plant of claim 2.
4. A lettuce plant having all the physiological and morphological characteristics of the lettuce plant of claim 2.
5. An $F_1$ hybrid lettuce plant having 'Crispers' as a parent where 'Crispers' is grown from the seed of claim 1.
6. Pollen of the plant of claim 2.
7. An ovule of the plant of claim 2.
8. Tissue culture of the plant of claim 2.
9. A method of selecting lettuce, comprising
   a) growing more than one plant from the seed of claim 1
   b) selecting a plant from step a).
10. A selected lettuce plant selected by the method of claim 9.
11. A lettuce seed produced from the selected plant of claim 10.

* * * * *